(12) United States Patent
Brückner et al.

(10) Patent No.: US 7,169,222 B2
(45) Date of Patent: Jan. 30, 2007

(54) MULTILAYER INTERFERENCE PIGMENTS

(75) Inventors: Hans-Dieter Brückner, Darmstadt (DE); Andrea Heyland, Reichelsheim (DE); Christoph Schmidt, Krifrel (DE); Christina Schank, Ober-Rarmstadt (DE); Claudia Seibel, Otzberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/177,322

(22) Filed: Jul. 11, 2005

(65) Prior Publication Data
US 2005/0241530 A1 Nov. 3, 2005

Related U.S. Application Data

(60) Continuation of application No. 10/757,456, filed on Jan. 15, 2004, now abandoned, which is a division of application No. 09/694,361, filed on Oct. 24, 2000, now Pat. No. 6,689,205, which is a continuation of application No. 09/230,262, filed as application No. PCT/EP97/02651 on May 23, 1997, now abandoned.

(51) Int. Cl.
C04B 14/00 (2006.01)
C04B 14/20 (2006.01)
C09C 1/04 (2006.01)
A01G 13/00 (2006.01)
A01G 7/00 (2006.01)

(52) U.S. Cl. .................. 106/400; 106/415; 106/417; 106/418; 106/428; 106/431; 106/436; 106/439; 47/2; 47/9; 47/29.1; 47/29.4

(58) Field of Classification Search ............... 106/415, 106/417, 418, 425, 428, 431, 436, 439, 400, 106/469; 47/2, 9, 29.1, 29.4
See application file for complete search history.

(56) References Cited

U.S. PATENT DOCUMENTS

| 3,071,482 A | 1/1963 | Miller et al. |
| 3,087,828 A | 4/1963 | Linton et al. |

(Continued)

FOREIGN PATENT DOCUMENTS

EP 370701 5/1990

(Continued)

OTHER PUBLICATIONS

Dorfner, K et al., Pearl Lustre Pigments-Characteristics and functional Effects, Specialty Chemicals (May 1982).

(Continued)

*Primary Examiner*—J. A. Lorengo
*Assistant Examiner*—Patricia L. Hailey
(74) *Attorney, Agent, or Firm*—Millen, White, Zelano & Branigan, P.C.

(57) ABSTRACT

Multilayer interference pigment consisting of a transparent carrier material coated with alternating layers of metal oxides of low and high refractive index, the difference in the refractive indices being at least 0.1, which is obtainable by alternate coating of the transparent carrier material with a metal oxide of high refractive index and with a metal oxide of low refractive index in a wet process by hydrolysis of the corresponding water-soluble metal compounds, separation, drying and, if desired, calcination of the resulting pigment.

12 Claims, 2 Drawing Sheets

U.S. PATENT DOCUMENTS

| Patent | Date | Inventor | Class |
|---|---|---|---|
| 3,123,490 A | 3/1964 | Bolomey et al. | |
| 3,138,475 A | 6/1964 | Schroder et al. | |
| 3,481,663 A | 12/1969 | Greenstein et al. | |
| 3,627,553 A | 12/1971 | Clark et al. | |
| 3,650,790 A | 3/1972 | Klenke et al. | |
| 3,767,443 A * | 10/1973 | Clark et al. | 106/415 |
| 3,858,977 A | 1/1975 | Baird et al. | |
| 4,010,293 A | 3/1977 | Davis | |
| 4,090,773 A | 5/1978 | Bauer et al. | |
| 4,151,666 A | 5/1979 | Rapheal et al. | |
| 4,168,986 A | 9/1979 | Venis et al. | |
| 4,232,079 A | 11/1980 | Raphael et al. | |
| 4,428,997 A | 1/1984 | Shulman et al. | |
| 4,481,254 A | 11/1984 | Fukushima et al. | |
| 4,531,765 A | 7/1985 | Shulman | |
| 4,545,648 A | 10/1985 | Shulman et al. | |
| 4,565,581 A | 1/1986 | Bernhard | |
| 4,653,775 A | 3/1987 | Rapheal et al. | |
| 4,867,793 A | 9/1989 | Franz et al. | |
| 4,879,140 A | 11/1989 | Gray et al. | |
| 4,882,143 A * | 11/1989 | Kadokura et al. | 424/59 |
| 4,920,692 A | 5/1990 | Kitamura et al. | |
| 5,075,195 A | 12/1991 | Babler et al. | |
| 5,091,011 A * | 2/1992 | DeLuca, Jr. | 106/417 |
| 5,364,467 A | 11/1994 | Schmid et al. | |
| 5,401,306 A * | 3/1995 | Schmid et al. | 106/417 |
| 5,607,504 A * | 3/1997 | Schmid et al. | 106/403 |
| 5,624,486 A | 4/1997 | Schmid et al. | |
| 5,767,179 A | 6/1998 | Takado | |
| 5,958,125 A | 9/1999 | Schmid et al. | |
| 5,993,526 A | 11/1999 | Sommer et al. | |
| 6,132,873 A | 10/2000 | Dietz et al. | |
| 6,156,115 A * | 12/2000 | Pfaff et al. | 106/403 |
| 6,284,032 B2 * | 9/2001 | Andes et al. | 106/436 |
| 6,500,251 B1 * | 12/2002 | Andes et al. | 106/415 |
| 6,602,340 B1 * | 8/2003 | Schank et al. | 106/415 |
| 6,630,018 B2 * | 10/2003 | Bauer et al. | 106/415 |
| 6,689,205 B1 * | 2/2004 | Bruckner et al. | 106/415 |
| 2004/0170838 A1 * | 9/2004 | Ambrosius et al. | 428/406 |

FOREIGN PATENT DOCUMENTS

| | | | |
|---|---|---|---|
| EP | 0711602 | | 1/1992 |
| EP | 708154 | | 4/1996 |
| EP | 0759566 | | 8/1996 |
| EP | 803552 | | 10/1997 |
| FR | 2429292 | | 1/1980 |
| JP | 57042756 | | 3/1982 |
| JP | 63126818 | | 5/1988 |
| JP | 63286343 | | 11/1988 |
| JP | 07-246366 | * | 9/1995 |
| WO | WO 94/05727 | * | 3/1994 |
| WO | WO 96/03029 | * | 2/1996 |
| WO | WO 98/12266 | | 3/1998 |

OTHER PUBLICATIONS

Derwent Publications Ltd., Week 9547, London, Great Britian, AN 95-363063, XP002051685 & JP 07246366A (Matsuda), Sep. 26, 1995.

Derwent Publications Ltd., Week 9413, London, Great Britian, AN 94-106716, XP002051514 & JP06056628A (Pola Chem. Ind. Inc.), Mar. 1, 1994.

Derwent Publications Ltd., Week 9009, London, Great Britian, AN 90-063308, XP002051513 & JP 02016168A (Kanebo Ltd.), Jan. 19, 1990.

Chemical Abstracts, vol. 110, No. 20, May 15, 1989, Columbus, Ohio, Abstract No. 176060y, Tsugita, Akira et al., APreparation of titania-alumina doubly coated mica powders and their optical properties@, XP000056533 & Shikizai Kyokaishi, Bd. 61, Nr. 12, 1988, Japan, pp. 685-691.

English Abstract for EP 803552.

English translation of Kokai No. Toku Kai Hei 7-246366, Application Date Jan. 17, 1995, Inventor: Kiwa Yamane, "A pearlescent Material and a Paint That Contains Same".

* cited by examiner

MULTILAYER INTERFERENCE PIGMENTS

This application is continuation of U.S. patent application Ser. No. 10/757,456 filed Jan. 15, 2004, now abandoned, which in turn is a divisional of U.S. patent application Ser. No. 09/694,361 filed Oct. 24, 2000, granted as U.S. Pat. No. 6,689,205, which in turn is a continuation of U.S. patent application Ser. No. 09/230,262, filed May 17, 1999, now abandoned, which is a 371 of PCT/EP97/02651 filed May 23, 1997.

The invention relates to multilayer interference pigments consisting of a transparent carrier material coated with alternating layers of a metal oxide of low refractive index and a metal oxide of high refractive index.

Multilayer pigments of low transparency and with a similar layer structure are known. The metal oxide layers are prepared either in a wet process, by precipitating the metal oxide hydrates from a metal salt solution onto a carrier material, or by vapour deposition or sputtering in a vacuum. In general, the vapour deposition processes are too complex and costly for mass production of pigments. Thus U.S. Pat. No. 4,434,010 describes a multilayer interference pigment consisting of a central layer or a reflecting material (aluminium) and alternating layers of two transparent, dielectric materials of high and low refractive index, for example titanium dioxide and silicon dioxide, either side of the central aluminium layer. This pigment is employed for the printing of securities.

JP H7-759 (Kokoku) describes a multilayer interference pigment with a metallic lustre. It consists of a substrate coated with alternating layers of titanium dioxide and silicon dioxide. The substrate is formed from flakes of aluminium, gold or silver or from platelets of mica and glass which are coated with metals. Accordingly, it is a typical metallic pigment. This pigment is of high opacity. For applications where a high level of transparency of the pigmented material is required, as for example for agricultural films, the pigment is unsuitable. Furthermore, it has the disadvantage, that the depth effect typical of interference pigments is not produced since, owing to the high reflection of light at the metal layer which forms the core, pigment particles lying deeper in the application medium are unable to contribute to the optical appearance. The interference effect therefore remains limited to the layers located on the metal layer.

The object of the invention is to provide an essentially transparent interference pigment having strong interference colours and/or a strong angular dependency of the interference colours. Furthermore, the object of the invention is to provide pigments having specific spectral characteristics in the visible region and in the infrared region.

This object is achieved in accordance with the invention by a multilayer interference pigment consisting of a transparent carrier material coated with alternating layers of metal oxides of low and high refractive index, the difference in the refractive indices being at least 0.1, which is obtainable by alternate coating of the transparent carrier material with a metal oxide of high refractive index and with a metal oxide of low refractive index in a wet process by hydrolysis of the corresponding water-soluble metal compounds, separation, drying and, if desired, calcination of the resulting pigment.

The transparent carrier material is mica, a different phyllosilicate, glass flakes, $PbCO_3 \times Pb(OH)_2$ and BiOCl in platelet form, or plateletlike silicon dioxide prepared by the process described in WO 93/08237.

The metal oxide of high refractive index can be an oxide or mixtures of oxides with or without absorbing properties, such as $TiO_2$, $ZrO_2$, $Fe_2O_3$, $Fe_3O_4$, $Cr_2O_3$, or ZnO, for example, or a compound of high refractive index, for example iron titanates, iron oxide hydrates and titanium suboxides, or mixtures and/or mixed phases of these compounds with one another or with other metal oxides.

The metal oxide of low refractive index is $SiO_2$, $Al_2O_3$, AlOOH, $B_2O_3$ or a mixture thereof and can likewise have absorbing or nonabsorbing properties. If desired, the oxide layer of low refractive index may include alkali metal oxides and alkaline earth metal oxides as constituents.

This object is additionally achieved in accordance with the invention by a process for the preparation of the novel pigments, in which the transparent carrier material is suspended in water and coated in alternation with a metal oxide hydrate of high refractive index and with a metal oxide hydrate of low refractive index by addition and hydrolysis of the corresponding water-soluble metal compounds, the pH necessary for the precipitation of the respective metal oxide hydrate being established and held constant by simultaneous addition of acid or base, and then the coated carrier material is separated off from the aqueous suspension, dried and, if desired, calcined.

The invention additionally relates to the use of the novel pigments for pigmenting paints, printing inks, plastics, glazes for ceramics and glass, cosmetics and, in particular, for the production of agricultural films.

For this purpose they can be employed as mixtures with customary commercial pigments, for example inorganic and organic absorption pigments, metallic pigments and LCP pigments.

The thickness of the layers of the metal oxides of high and low refractive index is critical for the optical properties of the pigment. Since a product with powerful interference colours is desired, the thicknesses of the layers must be adjusted relative to one another. If n is the refractive index of a layer and d its thickness, the interference colour of a thin layer is the product of n and d, i.e. the optical thickness. The colours of such a film, as produced with normal incidence of light in reflected light, result from an intensification of the light of wavelength $\lambda=(4/2N-1) \cdot nd$ and by attenuation of light of wavelength $\lambda=(2/N) \cdot nd$, where N is a positive integer. The variation in colour which takes place as the thickness of the film increases results from the intensification or attenuation of particular wavelengths of the light by interference. For example, a 115 nm film of titanium dioxide of refractive index 1.94 has an optical thickness of 115×1.94=223 nm, and light of wavelength 2×223 nm=446 nm (blue) is attenuated in the course of reflection, with the result that the reflected light is yellow. In the case of multilayer pigments, the interference-colour is determined, by the intensification of specific wavelengths and, if two or more layers in a multilayer pigment possess the same optical thickness, the colour of the reflected light becomes more intense and full as the number of layers increases. Moreover, by a suitable choice of the layer thicknesses it is possible to achieve a particularly marked variation of colour in dependency on the viewing angle. A pronounced colour flop develops, which may be desirable for the pigments according to the invention. The thickness of the individual metal oxide layers, independently of their refractive index, is therefore from 20 to 500 nm, preferably from 50 to 300 nm.

The number and thickness of the layers is dependent on the desired effect and on the substrate used. On mica, the desired effects are achieved if the 3-coat system $TiO_2/SiO_2/TiO_2$ is built up and if the thicknesses of the individual layers are matched optically to one another. When using optically relatively thin $TiO_2$ and $SiO_2$ layers (layer thickness <100 nm) it is possible, for example, to produce pigments with a blue interference colour which, with a substantially smaller $TiO_2$ content, are stronger in colour and more transparent than pure $TiO_2$-mica pigments. The saving in terms of $TiO_2$ is up to 50% by weight.

By means of the precipitation of thick $SiO_2$ layers (layer thickness >100 nm), pigments having a strongly pronounced angular dependency of the interference colour are obtained.

By precipitating further $TiO_2$ and $SiO_2$ layers it is also possible to obtain 5-layer and higher systems, but then the number of layers is limited by the economics of the pigment.

However, if $SiO_2$ platelets of uniform layer thickness are used as substrate instead of mica, then further, particularly well-defined interference effects can be achieved.

In this case, covering the substrate with, for example, 3 layers of the abovementioned structure produces an interference system comprising 7 thin layers of sharply defined thicknesses. The reflection or transmission spectrum of such a pigment exhibits finer and more precisely matchable structures than the spectrum of a corresponding pigment based on a substrate with a broad distribution of thickness, such as mica.

Even with extremely thin $TiO_2$ layers (layer thickness <50 nm), these pigments exhibit powerful interference colours. The angular dependency of the interference colour is also particularly pronounced. This extreme colour flop is not observed with conventional metal oxide-mica pigments.

The $SiO_2$ platelets are prepared, for example, in accordance with international application WO 93/08237 on a continuous belt by solidification and hydrolysis of an alkali metal silicate solution.

The metal oxide layers are preferably applied by a wet-chemical process which may be one of those wet-chemical coating processes developed for the preparation of pearl lustre pigments; processes of this kind are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602 and DE 32 35 017 or else in further patent documents and other publications.

For the coating, the substrate particles are suspended in water, and one or more hydrolysable metal salts are added at a pH which is suitable for the hydrolysis and is chosen so that the metal oxides and/or metal oxide hydrates are precipitated directly onto the particles without any instances of secondary precipitation. The pH is usually kept constant by simultaneous metered addition of a base. The pigments are then separated off, washed and dried and, if desired, calcined, it being possible to optimize the calcining temperature with respect to the particular coating present. If desired, pigments to which individual coatings have been applied can be separated off, dried and, if desired, calcined before being resuspended in order to apply the further layers by precipitation.

Furthermore, coating can also be carried out in a fluidized-bed reactor by gas phase coating, in which context it is possible, for example, to employ correspondingly the techniques proposed for the preparation of pearl lustre pigments in EP 0 045 851 and EP 0 106 235.

The metal oxide of high refractive index used is Preferably titanium dioxide, and the metal oxide of low refractive index preferably used is silicon dioxide.

For the application of the titanium dioxide layers the process described in U.S. Pat. No. 3,553,001 is preferred.

An aqueous titanium salt solution is added slowly to a suspension, heated to about 50–100° C., in particular 70–80° C., of the material to be coated, and a substantially constant pH of about 0.5–5, in particular about 1.5–2.5, is maintained by simultaneous metered addition of a base, for example aqueous ammonia solution or aqueous alkali metal hydroxide solution. As soon as the desired layer thickness of the $TiO_2$ precipitation has been reached, the addition of the titanium salt solution and of the base is stopped.

This process, also termed the titration process, is notable for the fact that it avoids an excess of titanium salt. This is achieved by supplying to the hydrolysis only that quantity per unit time which is necessary for uniform coating with the hydrated $TiO_2$ and which can be received per unit time by the available surface area of the particles to be coated. There is therefore no production of hydrated titanium dioxide particles not precipitated on the surface to be coated.

For the application of the silicon dioxide layers, the following process can be employed: a sodium silicate solution is metered into a suspension, heated to about 50–100° C., in particular 70–80° C., of the material to be coated. The pH is held constant at 4–10, preferably at 6.5–8.5, by simultaneous addition of 10% hydrochloric acid. Stirring is carried out for 30 minutes following addition or the silicate solution.

It is also possible to alter the powder colour of the pigment by applying further layers, for example coloured metal oxides or Prussian blue, transition metal compounds, such as compounds of Fe, Cu, Ni, Co or Cr, for example, or organic compounds such as dyes or colour lakes.

The wet-chemical production of 2 or more interference layers of different refractive index with precisely defined thicknesses on finely divided plateletlike substrates in an aqueous medium using purely inorganic starting materials has not been disclosed hitherto.

It is additionally possible to subject the finished pigment to an aftercoating or aftertreatment process which further increases the stability to light, weather and chemicals, or which facilitates the handling of the pigment, especially its incorporation into different media. Suitable aftercoating and aftertreatment processes are those described, for example, in DE-C 22 15 191, DE-A 31 51 354, DE-A 32 35 017 or DE-A 33 34 598.

The substances additionally applied make up only about 0.1–5% by weight, preferably about 0.5–3% by weight, of the overall pigment.

In addition, the novel pigment can also be coated with thermally adhering inorganic or organic colorants of low solubility. Preference is given to the use of colour lakes and, in particular, aluminium colour lakes. For this purpose a layer of aluminium hydroxide is applied by precipitation and in a second step is laked with a colour lake. The process is described in more detail in DE 24 29 762 and DE 29 28 287.

Preference is also given to an additional coating with complex salt pigments, especially cyanoferrate complexes, for example Prussian blue and Turnbull's blue, as is described in EP 0 141 173 and DE 23 13 332.

The novel pigment can also be coated with organic dyes and, in particular, with phthalocyanine or metal phthalocyanine and/or indanthrene dyes in accordance with DE 40 09 567. To this end a suspension of the pigment in a solution of the dye is prepared and this solution is then brought together with a solvent in which the dye is of low or zero solubility.

Furthermore, metal chalcogenides or metal chalcogenide hydrates and carbon black can also be employed for an additional coating.

The pigment can be used in a conventional manner for pigmenting paints, printing inks, plastics, cosmetics and glazes for ceramics and glass. It is preferably used for pigmenting agricultural films.

Agricultural films are often treated with pigments in order to keep out the infrared radiation of the sun and thus to prevent overheating in, for example, a greenhouse.

Almost all of the pigments used to date in agricultural films are colour pigments. Therefore, they absorb or reflect a substantial proportion of the visible light which, however, is required by the plants living under the film for their growth. As a consequence, the pigments used to date in agricultural films have an adverse effect on the growth behaviour of the plants.

It is therefore an object of the present invention to provide an interference pigment having high transmissibility in the visible region of light and high reflectivity in the NIR region. The properties of such pigments can also be adjusted so that they have other or additional functions, for example to influence the morphogenis of plants in a controlled manner.

The examples which follow are intended to illustrate the invention in more detail without limiting it.

EXAMPLE 1

3-Layer system with Thin $SiO_2$ Layer

Figure 1:
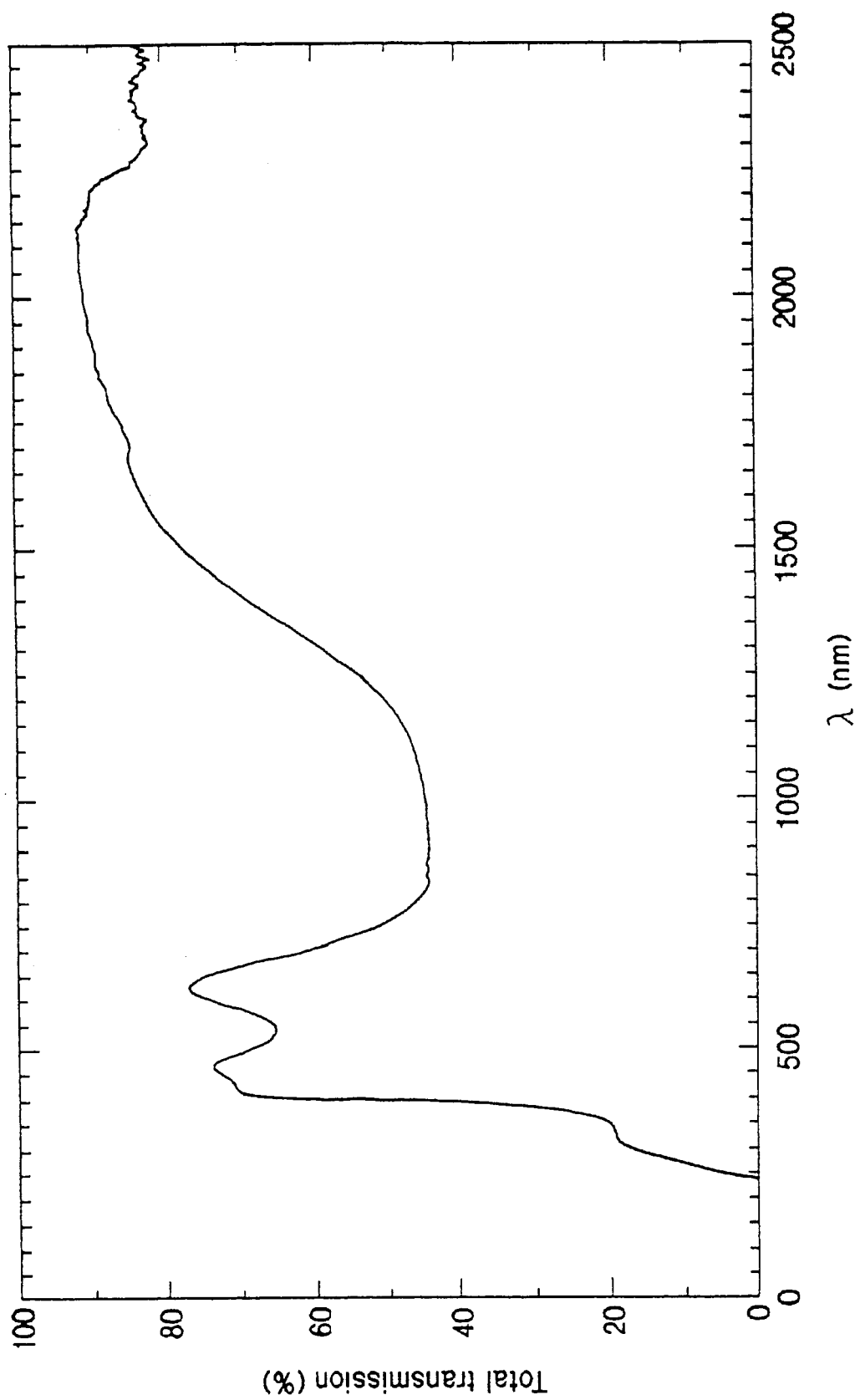
FIG. 1 represents the transmission spectrum of a paint film produced from the pigment of Example #5.

1) First $TiO_2$ Layer:

150 g of mica (particle size 10–40 μm) are suspended in 2 l of deionized water and the suspension is heated to 75° C. 175 ml of an aqueous $TiCl_4$ solution (400 g of $TiCl_4$) is metered into this suspension over the course of 60 minutes. Throughout the addition the pH is held constant at 2.2 with 32% NaOH solution. When addition is over, stirring is carried out at 75° C. for 30 minutes in order to complete the precipitation.

2) $SiO_2$ Layer:

The pH of the suspension is raised to 7.5 with NaOH solution, and 250 ml of a sodium silicate solution (125 g of $SiO_2$/l) are metered in at 75° C. over the course of 90 minutes. During this time, the pH is held constant with 10% hydrochloric acid. When addition is over, stirring is carried out at 75° C. for 30 minutes again in order to complete the precipitation.

3) Second $TiO_2$ Layer:

The pH is reduced again to 2.2 with 10% hydrochloric acid, and $TiO_2$ is again applied by precipitation from a further 175 ml of $TiCl_4$ solution, as described in step 1).

The mixture is then cooled to room temperature, and the pigment obtained is filtered off, washed salt-free with deionized water and dried at 110° C. The pigment is then calcined at 850° C. for 30 minutes.

The pigment thus obtained is notable for the more intense blue interference colour and higher transparency than comparable pure $TiO_2$-mica pigments.

EXAMPLE 2

3-Layer System with Thick $SiO_2$ Layer

1) First $TiO_2$ Layer:

150 g of mica (particle size 10–40 μm) are suspended in 2 l of deionized water and the suspension is heated to 75° C. 300 ml of an aqueous $TiCl_4$ solution (400 g of $TiCl_4$/l) is metered into this suspension over the course of 100 minutes. Throughout the addition the pH is held constant at 2.2 with 32% NaOH solution. When addition is over, stirring is carried out at 75° C. for 30 minutes in order to complete the precipitation.

2) $SiO_2$ Layer:

The pH of the suspension is raised to 7.5 with NaOH solution, and 1350 ml of a sodium silicate solution (125 g $SiO_2$/l) are metered in at 75° C. over the course of 7.5 hours. During this time, the pH is held constant with 10% hydrochloric acid. When addition is over, stirring is carried out at 75° C. for 30 minutes again in order to complete the precipitation.

3) Second $TiO_2$ Layer:

The pH is reduced again to 2.2, and $TiO_2$ is again applied by precipitation from a further 250 ml of $TiCl_4$ solution, as described in step 1).

The mixture is then cooled to room temperature, and the pigment obtained is filtered off, washed salt-free with deionized water and dried at 110° C. The pigment is then calcined at 850° C. for 30 minutes.

The pigment thus obtained when viewed straight on exhibits an intense blue-green interference colour which changes through violet into red when the pigment is tilted.

EXAMPLE 3

3-Layer System with $Fe_2O_3$ Layer

This example describes a layer structure in which the 3rd layer is not $TiO_2$ again but instead $Fe_2O_3$.

1) $TiO_2$ Layer:

As described in Example 1.

2) $SiO_2$ Layer:

As described in Example 1.

3) $Fe_2C_3$ Layer:

The pH of the suspension of the mica coated with $TiO_2$ and $SiO_2$ is adjusted to 3.0 using 10% hydrochloric acid. Then 1750 ml of an aqueous $FeCl_3$ soluton (35 g Fe/l) are metered in at 75° C. over the course of 5 hours while maintaining the pH at a constant level by simultaneous addition of 32% NaOH. Stirring is then carried out at 75° C. for 45 minutes in order to complete the precipitation.

The mixture is then cooled to room temperature, and the red-brown pigment obtained is filtered off, washed salt-free with deionized water and dried at 110° C. The pigment is then calcined at 850° C. or 30 minutes. An orange-brown pearl lustre pigment with a copper like interference colour is obtained.

EXAMPLE 4

Multilayer System Comprising 5 Alternating $TiO_2$ and $SiO_2$ Layers

As described in Example 1, mica is coated with $TiO_2$, $SiO$ and $TiO_2$. The another $SiO_2$ and a final $TiO_2$ layer are applied. Working up is as described above.

The pigment obtained has a clearer blue interference colour and higher transparency than that of Example 1.

EXAMPLE 5

3-Layer System with High Transparency in the Visible Region and High Reflection in the Near Infrared Region 100 g of mica (particle size 10–60 μm) are suspended in 2 l of deionized water and the suspension is heated to 80° C. with vigorous stirring. A solution of 3 g of $SnCl_4 \times 5H_2O$ and 10 ml of hydrochloric acid (37%) in 90 ml of deionized water is metered into this mixture at a pH of 2.0 and at a rate of 4 ml/min. Then, at a pH of 1.8, a quantity of 481 ml of $TiCl_4$ solution (400 g $TiCl_4$/l) is metered in at a rate of 2 ml/min. The pH is then adjusted to 7.5 with sodium hydroxide solution (32%) and, at this pH, a solution of 230 ml of sodium silicate (from Merck; Order No. 5621) in 314 ml of deionized water is metered in at a rate of 2 ml/min. The pH during this procedure is kept constant with hydrochloric acid (10%). Then, at a pH of 2.0, a solution of 3 g of $SnCl_4 \times 5H_2O$ and 10 ml of hydrochloric acid (32%) in 90 ml of deionized water is metered in at a rate of 4 ml/min. Then, at a pH of 1.8, 481 ml of $TiCl_4$ solution (400 g $TiCl_4$/l) are metered in at a rate of 2 ml/min.

The pH is held constant, in each case with NaOH solution (32%), during the addition of $SnCl_4 \times 5H_2O$ solutions and $TiCl_4$ solutions.

For working up, the pigment is filtered off, washed with 20 l of deionized water, dried at 110° C. and calcined at 850° C. for 30 minutes.

This pigment was used to produce a paint film whose transmission spectrum is reproduced in FIG. 1. The pigment is notable for a very good transparency in the visible region of light and a very high reflection in the near infrared region, properties which cannot be achieved with conventional interference pigments. Consequently, this pigment is particularly suitable for use in agricultural films.

EXAMPLE 6

Pigment with High Angular Dependency of the Colour 100 g of a $TiO_2$-mica pigment (particle size 10–60 μm, 35% $TiO_2$) are suspended in 2 l of deionized water and the suspension is heated to 80° C. with vigorous stirring. The pH is then adjusted to 7.5 with sodium hydroxide solution (32%) and, at this pH, a solution of 296 ml of sodium silicate (from Merck; Order No. 5621) in 300 ml of deionized water is metered in at a rate of 2 ml/min. During this addition, the pH is held constant with hydrochloric acid (10%). Then, at a pH of 2.0, a solution of 3 g of $SnCl_4 \times 5H_2O$ and 10 ml of hydrochloric acid (37%) in 90 ml of deionized water is metered into this mixture at a rate of 4 ml/min. Subsequently, at a pH of 1.8, a quantity of 238 ml of $TiCl_4$ solution (400 g $TiCl_4$/l) is metered in at a rate of 2 ml/min.

The pH is kept constant, in each case using NaOH solution (32%), during the addition of the $SnCl_4 \times 5H_2O$ solution and the $TiCl_4$ solution.

For working up the pigment is filtered off, washed with 20 l deionized-water, dried at 110° C. and calcined at 850° C. for 30 minutes.

The calcined pigment is stirred into a clear-coat (concentration 1.7%) which is applied to a black/white card.

Figure 2:
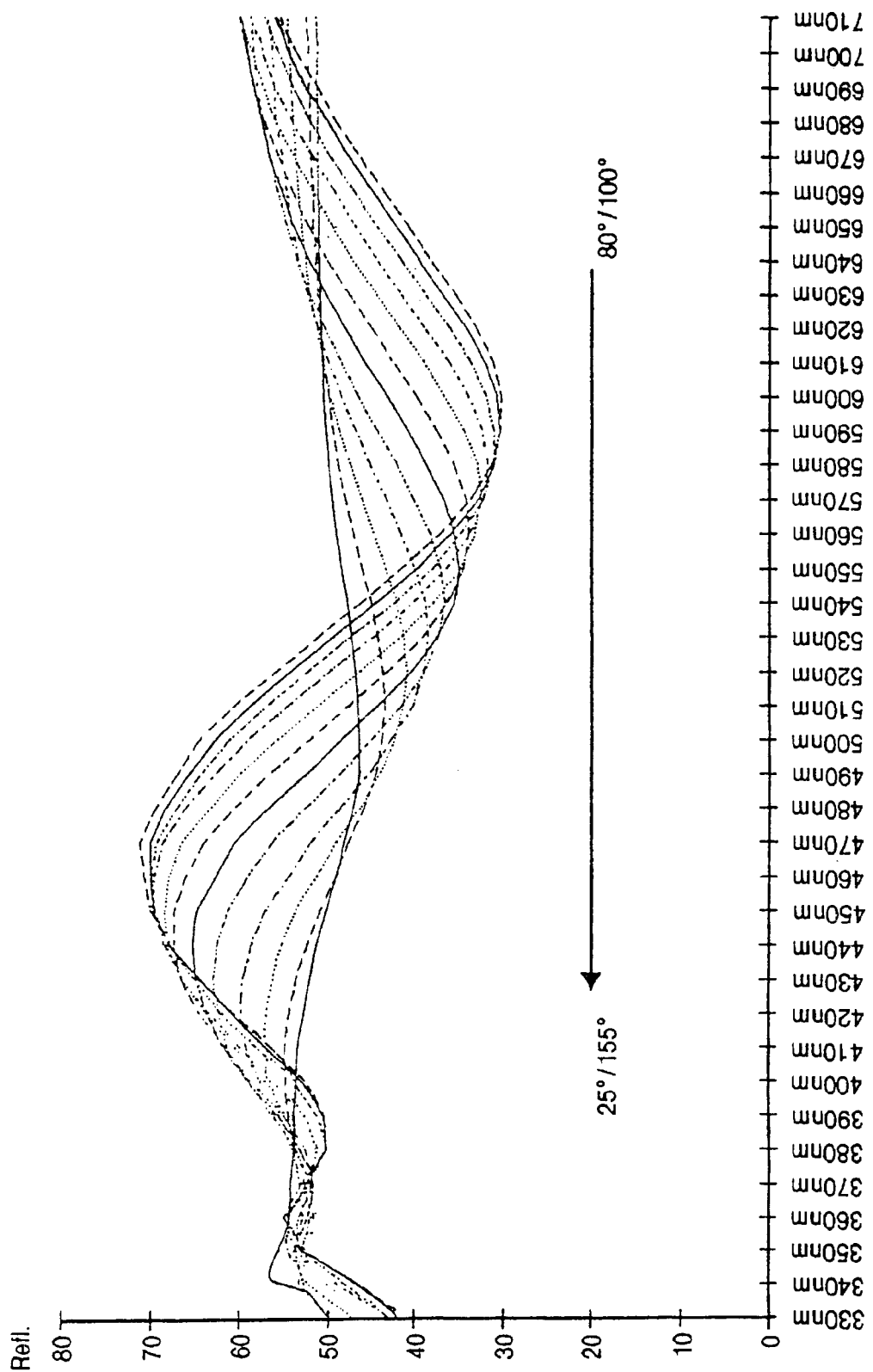
FIG. 2 represents the reflection spectrum of a pigment produced in Example #6.

The interference colour of the pigment is very much in evidence, especially on the black card. When the card is tilted from a steep to a flat viewing angle, the reflected colour changes from intense blue to intense violet. The reflection spectrum of the black card was measured under various steep (80°/100°) and flat (25°/1550°) observation angles. The reflection curves are reproduced in FIG. 2.

EXAMPLE 7

3-Layer System with $SiO_2$ Platelets as Carrier Material

1) First $TiO_2$ Layer:

100 g of $SiO_2$ platelets (particle size 20–70 μm) are suspended in 1.5 l of deionized water and the suspension is heated to 75° C. 160 ml of an aqueous $TiCl_4$ solution (400 g of $TiCl_4$/l) is metered into this suspension over the course of 90 minutes. Throughout the addition the pH is held constant at 2.2 with 32% NaOH solution. When addition is over, stirring is carried out at 75° C. for 30 minutes in order to complete the precipitation.

2) $SiO_2$ Layer:

The pH of the suspension is raised to 7.5 with NaOH solution, and 720 ml of a sodium silicate solution (125 g of $SiO_2$/l) are metered in at 75° C. over the course of 3.5 h. During this time, the pH is held constant with 10% hydrochloric acid. When addition is over, stirring is carried out at 70° C. for 30 minutes again in order to complete the precipitation.

3) Second $TiO_2$ Layer:

The pH is reduced again to 2.2 and $TiO_2$ is again applied by precipitation from a further 235 ml of $TiCl_4$ solution, as described in step 1).

The mixture is then cooled to room temperature, and the pigment obtained is filtered off, washed salt-free with deionized water and dried at 110° C. The pigment is then calcined at 850° C. for 30 minutes. The pigment thus obtained, when viewed straight on, exhibits a brilliant yellow-green interference colour which changes through blue-green to dark violet when the pigment is tilted.

The invention claimed is:

1. An agricultural film, comprising a multi-layer interference pigment comprising a transparent carrier material coated with a first layer of a high refractive index material, and thereon alternating layers of colorless low refractive index material then high refractive index material, the difference in refractive indices being at least 0.1, wherein the layers of high refractive index material consist of a non-absorbing colorless oxide or mixtures thereof, the pigment having high transmissibility in the visible region of light, and high reflectivity in the near infrared region, wherein the multilayer interference pigment is prepared by alternate coating of the transparent carrier material with a metal oxide of high refractive index and with a metal oxide of low refractive index in a wet process by hydrolysis of corresponding inorganic water-soluble metal compounds, separation, drying and optional calcination of resulting pigment, wherein the oxide of high refractive index consists of a non-absorbing colorless oxide or mixture of such oxides, and wherein the low refractive index material is colorless.

2. An agricultural film according to claim 1, wherein in the pigment the transparent carrier material is mica, a phyllosilicate, glass flakes, $PbCO_3 \times Pb(OH)_2$, BiOCI or platelet shaped $SiO_2$.

3. An agricultural film according to claim 1, wherein in the pigment the material of the high refractive index layers is $TiO_2$, $ZrO_2$, ZnO or a mixture of these oxides.

4. An agricultural film according to claim 1, wherein in the pigment the layer of low refractive index material is $SiO_2$, $Al_2O_3$, AlOOH, $B_2O_3$ or a mixture thereof, and the layer optionally further comprises alkali metal oxides or alkaline earth metal oxides.

5. A process for the preparation of an agricultural film according to claim 1, comprising processing the multi-layer interference pigment into a film to form an agricultural film, wherein the pigment is prepared by a process comprising suspending the transparent carrier material in water and coating alternately with a colorless metal oxide hydrate of high refractive index and with a colorless metal oxide hydrate of low refractive index by addition and hydrolysis of the corresponding water-soluble metal compounds, the pH for the precipitation of the metal oxide hydrates being established and held constant by addition of acid or base, and suspending coated carrier material off from aqueous suspension, drying and optionally calcining, wherein the resultant oxide of high refractive index consists of a non-absorbing colorless oxide or mixture of such oxides and the resultant oxide of low refractive index consists of colorless oxide or mixture of such oxides.

6. A process according to claim 5, wherein the transparent carrier material employed is mica, a phyllosilicate, $PbCO_3 \times Pb(OH)_2$, BiOCl or platelet shaped $SiO_2$.

7. A process according to claim 5, wherein the metal oxide of high refractive index is $TiO_2$, $ZrO_2$, or ZnO.

8. A process according to claim 5, wherein the metal oxide of low refractive index is $SiO_2$, $Al_2O_3$, AlOOH, $B_2O_3$ or a mixture thereof, and optionally further comprising alkali metal oxides or alkaline earth metal oxides.

9. An agricultural film according to claim 1, wherein in the pigment the transparent carrier material is mica and the mica is coated with a first layer of $TiO_2$ a second layer of $SiO_2$, and a third layer of $TiO_2$.

10. An agricultural film according to claim 1, wherein in the pigment the transparent carrier material is silica and the silica is coated with a first layer of $TiO_2$, a second layer of $SiO_2$, and a third layer of $TiO_2$.

11. An agricultural film according to claim 1, wherein in the pigment the carrier material is coated on each side.

12. An agricultural film comprising a multi-layer interference pigment comprising a transparent carrier material coated with a first layer of a high refractive index material, and thereon alternating layers of a colorless low refractive index material and high refractive index material, the difference in refractive indices being at least 0.1, wherein the high refractive index material alternating with the low refractive index material is ZnO, $TiO_2$ or $ZrO_2$.

* * * * *